United States Patent [19]

Zanetti

[11] Patent Number: 4,750,487
[45] Date of Patent: Jun. 14, 1988

[54] STEREOTACTIC FRAME

[76] Inventor: Paul H. Zanetti, 5226 St. Andrews, Corpus Christi, Tex. 78413

[21] Appl. No.: 934,116

[22] Filed: Nov. 24, 1986

[51] Int. Cl.⁴ ............................................. A61B 17/00
[52] U.S. Cl. ................................. 128/303 B; 378/162; 269/328
[58] Field of Search ...................... 128/303 B, 314, 315, 128/329; 33/257, 260; 378/162, 163, 164; 269/1, 2, 328

[56] References Cited

U.S. PATENT DOCUMENTS

| | | | |
|---|---|---|---|
| 1,370,640 | 3/1921 | Granger | 378/163 |
| 2,526,988 | 10/1950 | Worden et al. | 378/164 |
| 2,711,738 | 6/1955 | Kelley et al. | 128/314 |
| 3,669,118 | 6/1972 | Colon-Morales | 128/361 |
| 4,467,791 | 8/1984 | Cabrera et al. | 128/303 B |
| 4,485,815 | 12/1984 | Amplatz | 128/329 R |
| 4,527,569 | 7/1985 | Kolb | 128/660 |

Primary Examiner—Dalton L. Truluck
Assistant Examiner—Denise Whelton
Attorney, Agent, or Firm—Blakely, Sokoloff, Taylor & Zafman

[57] ABSTRACT

A stereo tactic frame for use with fluoroscopy is utilized to aim and guide a puncturing tool to a target located within a body. An aperture within the frame is positioned to overlie the target when viewed on a fluoroscopic image display. The frame is then rotated about two axes so that the aperture plane is made perpendicular to the beam passing through the aperture, wherein the center of the aperture is made to align with the target object.

9 Claims, 5 Drawing Sheets

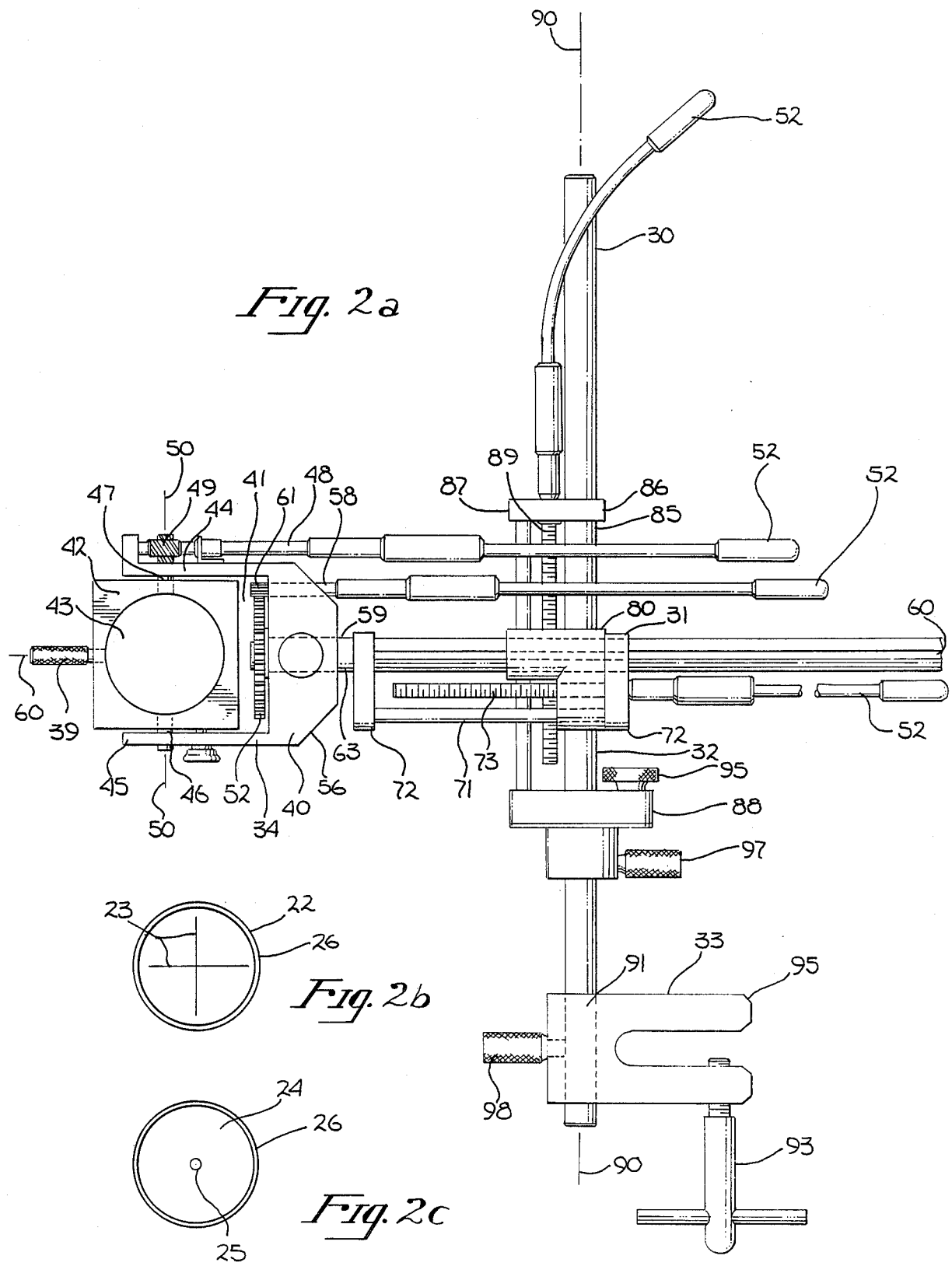

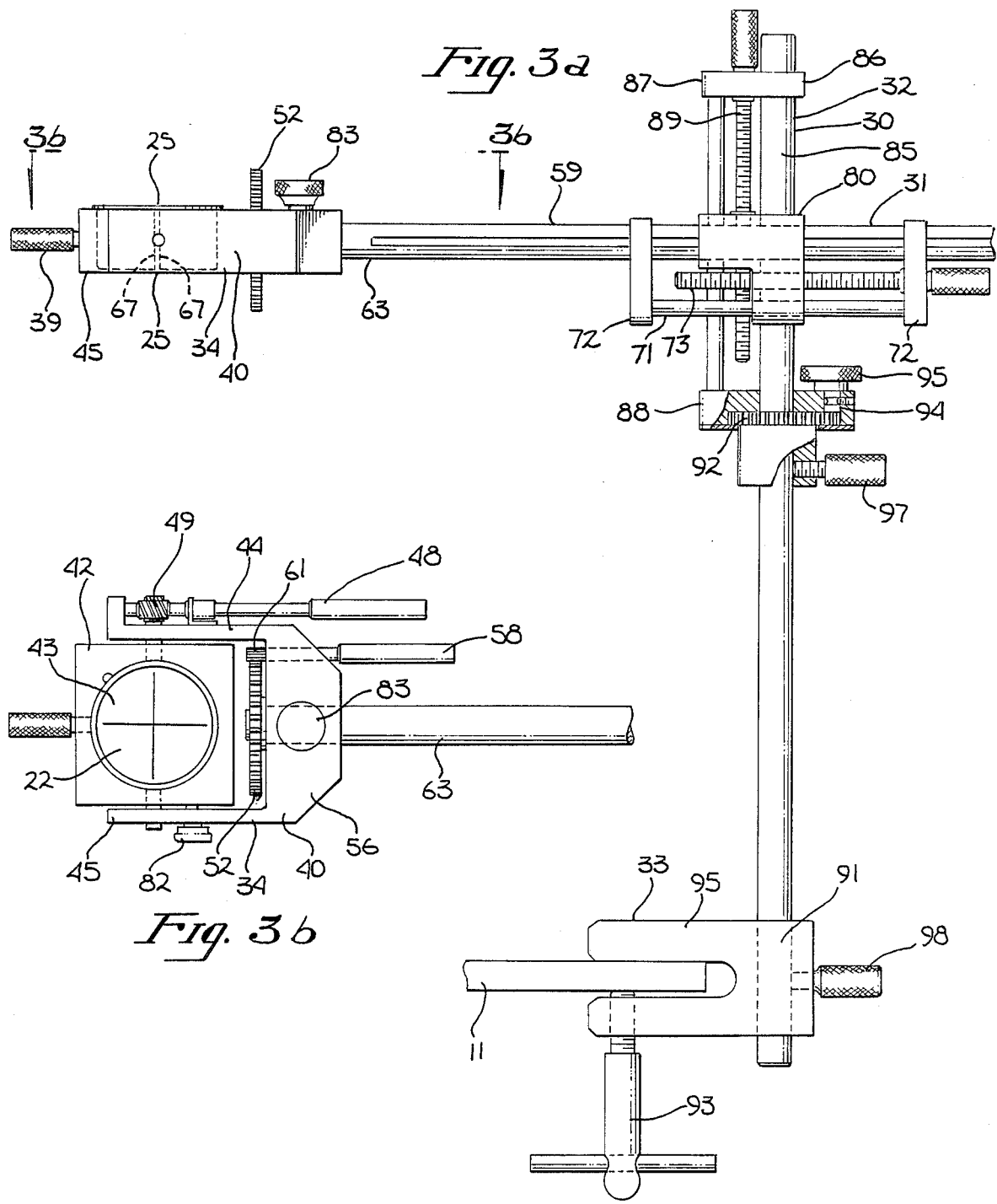

STEREOTACTIC FRAME

BACKGROUND OF THE INVENTION

I. Field of the Invention

The present invention relates to a field of medical instrumentation and, more specifically, to an apparatus for aiming a needle when such needle is used in penetrating a body to reach an internal object.

II. Prior Art

The use of a needle to penetrate a human body is a well-known medical practice. Some typical uses for such needle penetration are for injections, removal of body tissues and fluids, and diagnostic probing. When a specific internal area is targeted as the destination of the needle, some means must be used to determine the disposition of the needle once it is in the body cavity.

One such procedure utilizes a fluoroscope. An x-ray beam is projected through the body and a fluoroscope is used as a receptor of the passed beam. The collected beam is intensified and then processed for video display. The resultant image is projected on to a viewing screen. The image presented by the x-ray scan provides a two-dimensional picture on the screen. Structures, such as bones, obstruct the passage of the x-ray beam and present a more distinct image on the display. Vascular structures, on the other hand, are only transiently opacified by the injection of a dye. Then the needle is inserted into the body at an angle from the access of the beam such that the distal point of the needle can be guided to the target by viewing the display screen.

However, free hand needle puncture of small targets under fluoroscopic control may require multiple needle passes to properly reach the target. The difficulty arises because the person performing the penetration must simultaneously observe the screen to determine the progress. This free hand procedure is further complicated because the three-dimensional penetration is being observed as a two-dimensional image. The freehand procedure is time consuming due to its trial-and-error technique of reaching the target.

It is appreciated that what is needed is a more objective approach of accurately reaching the target by requiring only a single pass of the needle.

SUMMARY OF THE INVENTION

A stereotactic frame for use with fluoroscopy to aim, align and guide a puncturing tool to a target located within a body is described. The frame device includes a head assembly which houses a sighting aperture. A linear X-Y translation mechanism and a pivotal rod are used to initially place the head assembly to overlie the target.

An X-ray beam is directed through the aperture and the target and the passed beam is received by an image intensifier for display onto a viewing screen. Cross-hairs in the aperture are used to sight in the target. The cross-hairs are then replaced with a holder containing a metal tube.

Then, gears in the head assembly are used to rotate the assembly along two perpendicular axes of the circular aperture until a perfect circle image of the tubing is displayed on the screen, therein assuring straight-line alignment of the center of the aperture to the target.

The puncturing tool is inserted through the center of the aperture to penetrate to the target. A different angle of fluoroscopy is then used to monitor the depth of the penetration of the puncturing tool.

BRIEF DESCRIPTION OF THE DRAWINGS

FIG. 2a is a plan view of the preferred embodiment.

FIG. 2b is an elevation view of a cross-hair sighting insert used in the preferred embodiment.

FIG. 2c is an elevation view of a holding insert used in the preferred embodiment.

FIG. 3a is a plan view showing a portion of the preferred embodiment and the use of the holding insert.

FIG. 3b is a plan view showing the frame assembly of the preferred embodiment along lines 3b—3b of FIG. 3a but showing the use of the cross-hair sighting insert.

FIG. 6b shows the displayed image from the procedure shown in FIG. 6a.

DETAILED DESCRIPTION OF THE PRESENT INVENTION

An invention is described which provides for an apparatus to be used in guiding a needle to its targeted objective within a body cavity. In the following description, numerous specific details are set forth such as specific structures in order to provide a thorough understanding of the present invention. It will be obvious, however, to one skilled in the art that the present invention may be practiced without these specific details. Also, well known medical procedures have not been described in detail in order not to unnecessarily obscure the present invention.

Figure 1A:
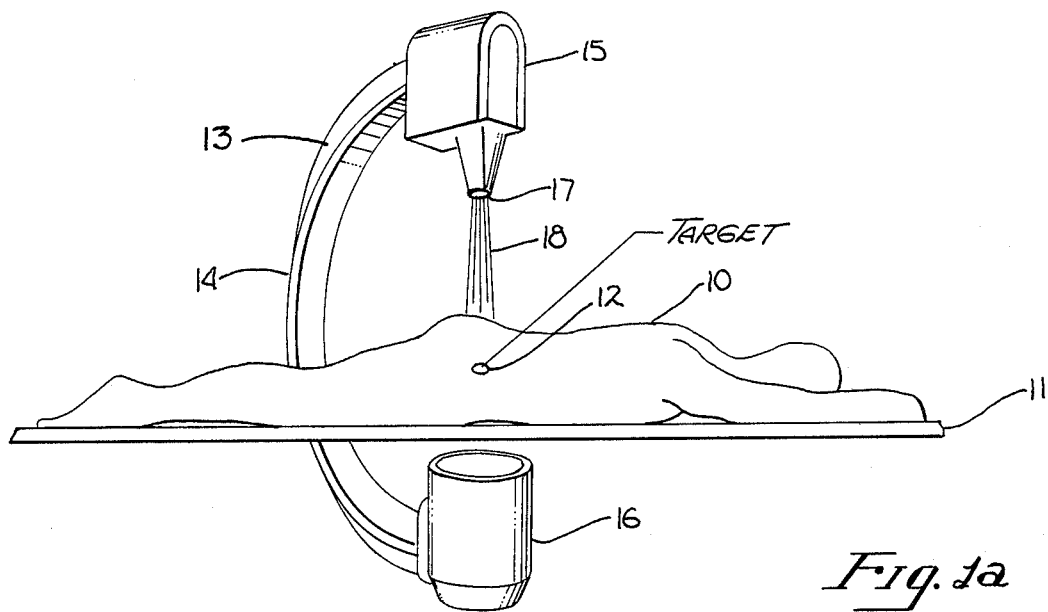
FIG. 1a is a pictorial illustration of using fluoroscopy to image internal objects of a body.

Referring to FIG. 1a, patient 10 is shown lying on a table top 11 and target 12 is shown to represent the targeted object within patient 10. A C-arm image intensifier 13 is shown having a C-arm 14 an x-ray projector 15 and a flouroscope 16. The projector 15 functions to generate an x-ray beam from the projection end 17. The C-arm image intensifier 13 is placed in position such that patient 10 is placed between projector 15 and fluoroscope 16. When intensifier 13 is activated to emit an x-ray beam 18 from projection end 17, the x-ray beam 18 passes through body 10 and target 12. The x-ray beam may pass through the table 11, but table 11 is made transparent to the beam 18. The x-ray beam 18 passing through the body 10 is received by flouroscope 16. The collected beam is intensified and processed for video presentation in a matter well known in the prior art.

Figure 1B:
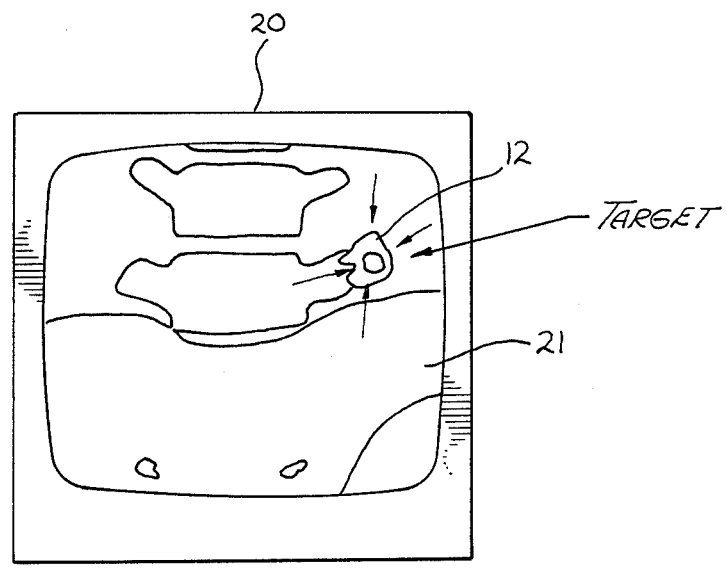
FIG. 1b is a fluoroscopic image as viewed on a viewing screen.

Also, referring to FIG. 1b, the received signals are processed to provide an image 21 on a video display screen 20. Initially, the patient 10 and C-arm image intensifier 13 are positioned approximately so that the desired sight of skin penetration overlies the target 12. The final positioning of the patient 10 is determined by positioning patient 10 and the C-arm image intensifier 13, such that target 12 is within a viewing area of image 21. The prior art practice at this point entailed free hand penetration of the needle by puncturing the skin of the patient 10 while watching screen 20 and observing the advance of the needle.

Referring to FIGS. 2a–c and 3a–b, a device 30 of the present invention which is used to sight and guide the needle to its predetermined target is shown. Device 30 is comprised of head assembly 34, horizontal translation assembly 31, vertical translation assembly 32, mounting assembly 33, and X-Y translation coupler 80.

Head assembly 34 is comprised of a U-shaped bracket 40 which has an opening end 41. A targeting frame 42 is inserted into opening 41. Targeting frame 42 has a circular aperture 43 disposed therein. In the preferred embodiment, targeting frame 42 is substantially a flat frame which fits into the U-shaped opening 41 of bracket 40. Frame 42 is coupled to the opposing sides 44 and 45 which form two of the sides of U-shaped bracket 40. The coupling of frame 42 to bracket 40 is accomplished by pins 46 and 47, and frame 42 rotates about pins 46 and 47 such that frame 42 swivels within opening 41. A shaft 48, having a worm gear 49 to drive pin 47 is attached to side 44 of bracket 40. Pin 47 extends through side 44 and mates with worm gear 49, wherein rotating shaft 48 causes mating pin 47 to also rotate, causing frame 42 to pivot about pins 46 and 47 within opening 41. Therefore, by rotating shaft 48, frame 42 will rotate about axis 50, axis 50 being coincident to a diameter of aperture 43, because pins 46 and 47 are in line with center of aperture 43.

A base 56 of U-shaped bracket 40 is coupled to an enlongated rod 59 of assembly 31. Rod 59 after passing through base 56 at bracket end 63 of the rod 59 also passes through the center of cog 52. Cog 52 is fixed to bracket 40, but rotates about rod 59. A shaft 58 passes through base 56 and is terminated by gear 61. Gear 61 mates with toothed cog 52, such that when shaft 58 is rotated, bracket 40 rotates about rod 59. Because the axis passing through the center of rod 59 is coincident to an axis 60 which forms a second diameter of aperture 43 and is also perpendicular to axis 50, frame 42 rotates in a second direction about axis 60, axis 60 being perpendicular to axis 50.

Rod 59 is part of horizontal translation assembly 31 which is comprised of rod 59, support rod 71, coupling members 72 and elongated screw shaft 73. Coupling members 72 couple rods 59 to 71 which are disposed substantially parallel. Shaft 73 passes through one of the coupling members 72 and is disposed between rods 59 and 71. Shaft 73, rods 59 and 71 pass through X-Y translation coupler 80 such that when screw shaft 73 is turned, assembly 31 moves horizontally within translation coupler 80 thereby allowing head assembly 34 to move horizontally along axis 60.

Vertical translation assembly 32 having rod 85, support rod 87, coupling members 86 and 88 to couple rods 85 and 87 which are substantially parallel. Screw shaft 89 passes through coupling member 86 and is disposed between rods 85 and 87. Vertical axis 90 is formed by the axis of rod 85. Assembly 32 is similar in construction to assembly 31. Shaft 89 and rods 85 and 87 pass through translation coupler 80 in a vertical direction which is perpendicular to the horizontal direction of assembly 31. Assemblies 31 and 32 are offset by coupler 80 so that interference between the two is prevented. By turning shaft 89, assembly 32 moves vertically along axis 90 in relation to translation coupler 80. Because axis 50 is parallel to axis 90, turning shaft 89 causes assembly 34 to travel along axis 50.

End 91 of rod 85 fits into and through clamp 95 of mounting assembly 33, such that rod 85 pivots about clamp 95. A wing screw 93 is used to tighten and lock clamp 95 when clamp 95 is attached to a fixed object such as table 11 of FIG. 1a. Rod 85 passes through cog gear 92 which is housed in member 88. A shaft 94, having knob 96 is geared to mate to gear 92 such that turning knob 96 causes rod 85 to rotate. A lock screw 97 when tightened prevents rotation of rod 85. A lock screw 98 is tightened to lock rod end 91 in clamp 95. Therefore, when assemblies 31 and 32 are made to move horizontally and vertically, the movements are in relation to the fixed object such as table 11.

It is appreciated that the preferred embodiment teaches one specific structure of the present invention. Various other structures may be suggested, as well as modifications implemented on the preferred embodiment, without departing from the spirit and scope of the invention.

Referring to FIGS. 2a–c, 3a–b, 4 and 5 the function of the stereotactic device 30 is shown in operation. Device 30 is fixed by mounting it onto a fixed assembly such as table 11 of FIG. 1, the mounting being accomplished by assembly 33. The patient 10 and C-arm image intensifier 13 are positioned so that the desired sight of skin penetration overlies the target 12. Frame 42 is then brought into fluoroscopic field by pivoting rod 85 about axis 60 by adjusting knob 95. Then, assembly 32 is adjusted for a vertical positioning along axis 90 and then assembly 31 is adjusted horizontally along axis 60. By working the above three adjustments, position of head assembly 34 is adjusted to overlie target 12 so that aperture 43 is approximately over the target when viewed on the display screen 20.

Figure 4:
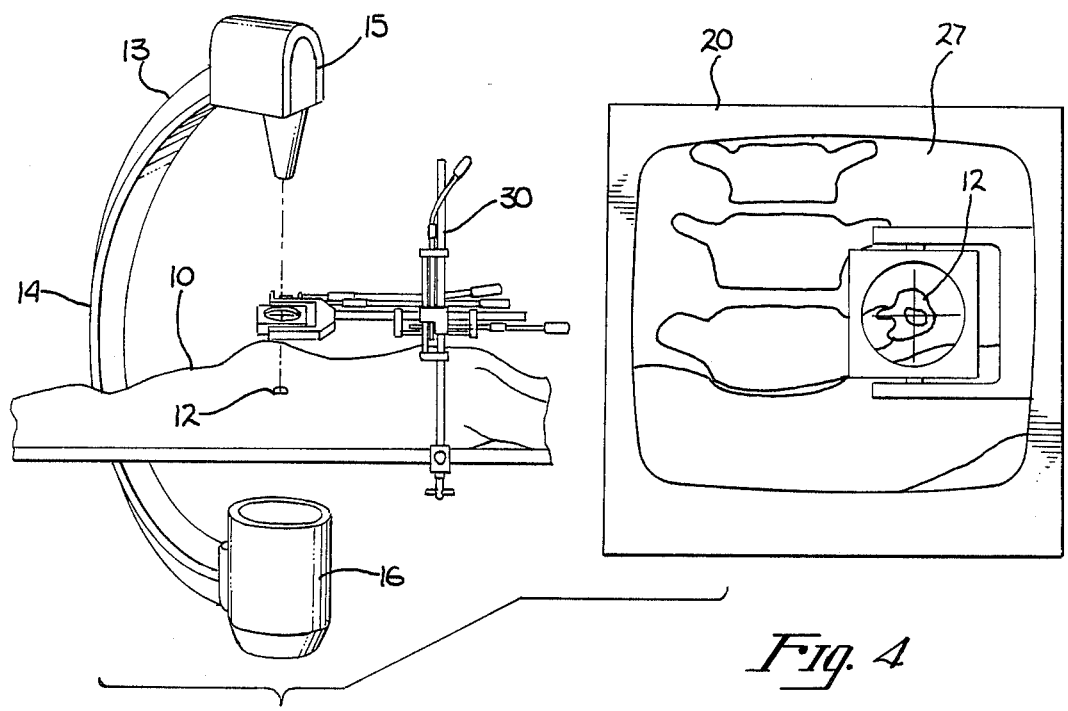
FIG. 4 shows the preferred embodiment in operation to sight a target and viewing it on a display screen by using the cross-hair sighting insert.
Figure 5:
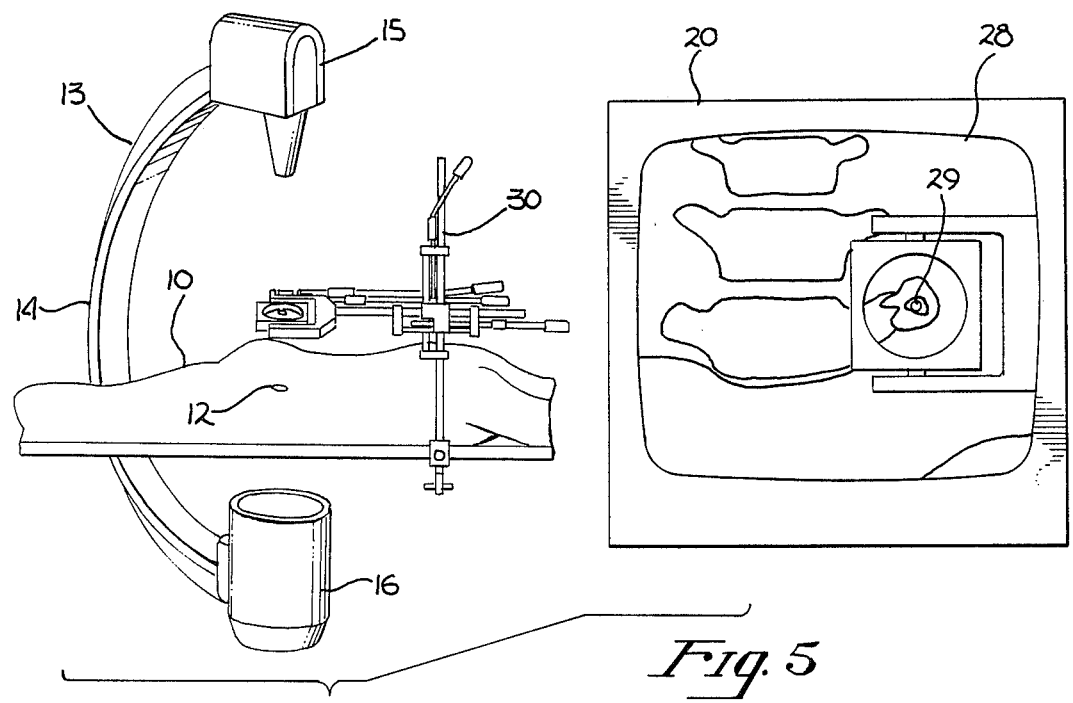
FIG. 5 shows the preferred embodiment in operation to align it to the target and viewing it on a display screen by using the holding insert.

Cross hair device 22 is inserted into the aperture 43 of frame 42. Device 22 is an insert and is shaped as a circular cup with lip 26 resting on frame 42. Device 22 is so constructed that cross-hairs 23 intersect at intersection of axes 50 and 60. The horizontal, vertical, and rotational gear drives are adjusted again as described above while viewing the cross-hairs 23 on the displayed image 27. Hence by repeated adjustment the cross hairs 23 are maneuvered under fluoroscopic imaging to overlie the target 12. The cross-hairs 23 are constructed of opaque material to fluoroscopy. The preferred embodiment uses metal wires. This adjustment procedure determines one point on the line through the target, that point being the position of aperture 43 along one plane formed by axes 50 and 60, wherein aperture 43 overlies the target in alignment with beam 18. This sighting procedure ends when cross-hairs 23 overlie the target 12 on image 27 as shown in FIG. 4.

Then the cross-hair device 23 is removed and holding device 24 is inserted into aperture 43 and locked into position by lock screw 39. Device 24 is constructed equivalently to device 22, except that device 24 has a center opening 25 instead of cross-hairs 23. Also, device 24 has an enclosed top such that a metal tube runs through the center from top to bottom, the tube being fixed within device 24 and being used as a guide. The tube is shown as dotted lines 67 on FIG. 3a and having opening 25. When device 24 is inserted into aperture 43, opening 25 will be positioned over the target, because opening 25 will coincide with the center of the cross-hairs 23 of device 22.

Next, shafts 48 and 58 are adjusted while viewing the image. When the imaged opening 29 appears as a perfect circle the alignment procedure is complete. Imaged opening 29 appears as a perfect circle when the plane of aperture 43 is normal to the beam 18 passing through the target 12 such that tube 67 is aligned with target 12. Device 24 has an opening 25 at the center which allows a puncturing device, such as a needle, to pass through the opening 25. A hardened metal tube 67 which is normal to the plane of the aperture 43 is incorporated in the device 24 of the preferred embodiment to permit opening 25 to guide the puncturing device. However, the present invention can be practiced without such metal tubing 67, because opening 25 can be aligned to the target by other in-line bore sighting techniques. Therefore, when imaged aperture 29 appears as a perfect circle, the length of the tube is aligned in a straight line to the target 12. Locks 82 and 83 are used to lock shafts 48 and 58.

Figure 6A:
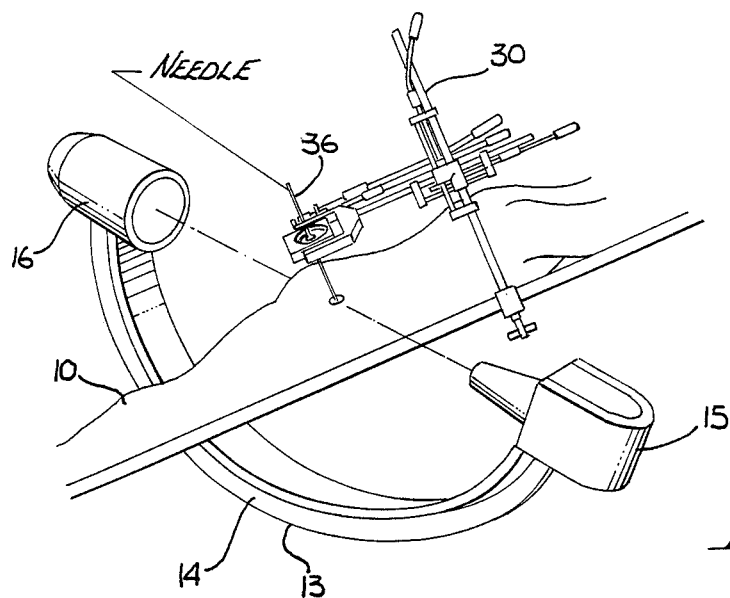
FIG. 6a is a pictorial illustration showing the penetration of a needle into the body and viewing it from a different angle.
Figure 6B:
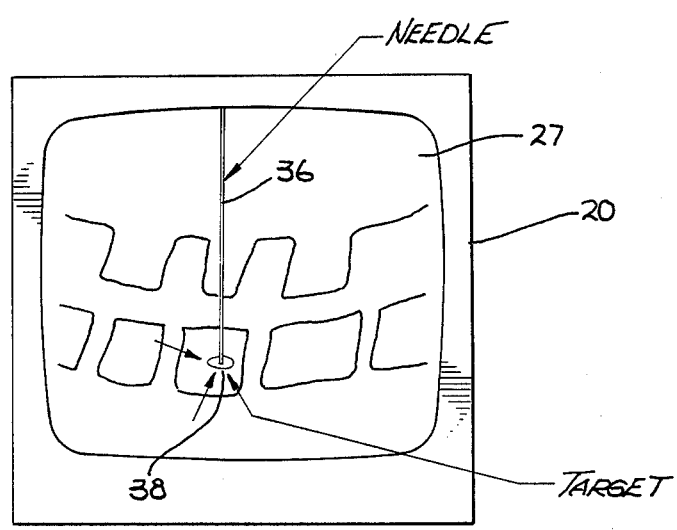

Referring to FIGS. 6a-b the C-arm image intensifier 13 is rotated at least 45° to another projection angle so that it can view the advancing of a needle 36 through the body. By viewing the fluoroscopic image display 37 the advancing point 38 of the needle 36 can be viewed to control the depth of penetration into patient. Because device 30 controls the proper alignment of the needle 36 to the target 12 by passing needle 36 through the tube of device 24, the procedure in FIGS. 6a-b permits accurate monitoring of the depth of penetration. The diameter of the tube of device 24 can be varied to accomodate various size needles.

The device 30 of the present invention provides an advantage of seeing a radiopque structure along the proposed needle pathway. Because device 30 facilitates the puncture of small vessles, it permits trans-needle embolization of some lesions in which satisfactory catheterization or freehand puncture of a feeding vessel is difficult to achieve. Therefore, puncture of a vascular structures is achieved by using the stored angiogram image with real-time road-mapping to accomplish the aiming.

Although actual dimensions are variable depending on use and the object to be viewed, the preferred embodiment has rods 59 and 85 which are approximately 16 inches long having diameters of 0.562 inches. Shafts 71 and 87 are five inches long and 0.250 inches in diameter. Bracket 40 is 3.5 inches across the base with the U-shaped opening being 2.625 inches wide. The frame 42 is 2.5 inches on each side and has a thickness of 1 inch. The aperture is two inches in diameter. It is apparent that the aperture diameter can be varied, even to the size of the tube opening. The two inch diameter is used so that the initial targeting is made easier.

The various assemblies 31, 32, 33, 34, and 80 are constructed from metal, although any structually hardened material may be used. Inserts 22 and 24 are constructed from non-opaque materials such as clear plastic, and insert 22 has bonded wires to form cross-hairs 23. Insert 24 has a metal tube therein. Further, the preferred embodiment uses flexible extensions 52, which are coupled to ends of shafts 48, 58, 73 and 89 to ease the access and manipulation of these shafts by the operator. It is to be appreciated that the present invention can be embodied in other forms, to accomplish the final objective of aiming and guiding a puncturing device to its target, without departing from the spirit and scope of the invention.

Thus a stereotactic frame for sighting and guiding a puncturing tool to a target is described.

I claim:

1. An apparatus for aiming a puncturing tool to a target, wherein said puncturing tool is guided to said target by viewing it on a fluoroscopic image display, comprising:
   a sighting member having an aperture which is an enlarged circular opening disposed throughout;
   a bracket coupled to said sighting member for supporting said sighting member;
   a translation means coupled to said bracket;
   mounting means coupled to said translation means for attachment to a fixed object;
   said translation means for providing movement of said apparatus relative to said fixed object;
   first rotating means coupled to said sighting member and said bracket for rotating said sighting member relative to said bracket and about a first axis formed by a first diameter of said circular opening;
   second rotating means coupled to said bracket and said translation means for rotating said bracket relative to said translation means, said rotation of said bracket causing said sighting member to also rotate about a second axis formed by a second diameter of said circular opening, said second diameter being perpendicular to said first diameter;
   said first and second rotating means include gears for providing said movement;
   said sighting member disposed to overlie on said target, wherein said first and second rotating means are manipulated such that a correct alignment of said sighting member is achieved when an x-ray beam passing through said sighting member to reach said target is perpendicular to said first and second axes;
   wherein alignment for said puncturing tool is provided.

2. The apparatus as defined in claim 1, wherein said apparatus is constructed from a metallic material.

3. An apparatus for aiming and guiding a puncturing tool to a target located within a body by viewing it on a fluoroscopic image display, comprising:
   an aiming frame having a circular aperture disposed throughout;
   a bracket coupled to said aiming frame for supporting said frame;
   an elongated horizontal member having a proximal end coupled to said bracket;
   a translation coupler coupled to said elongated horizontal member for providing slideable movement of said horizontal member along a horizontal direction which is parallel to a horizontal axis formed by a length of said elongated horizontal member;
   an elongated vertical member coupled to said translation coupler, said coupler providing slideable movement of said coupler along a vertical direction which is parallel to a vertical axis formed by a length of said elongated vertical member;
   mounting means coupled to a distal end of said elongated vertical member for attaching said distal end to a fixed object;
   first rotating means coupled to said frame and said bracket for rotating said frame relative to said bracket, such that said frame rotates about a first axis formed by a first diameter of said aperture;
   said first rotating means is comprised of a worm gear disposed along one side of said bracket, and said worm gear is coupled to a geared mating pin which is coupled to said frame to rotate said frame when said worm gear is rotated;

second rotating means coupled to said elongated horizontal member and said bracket for rotating said bracket relative to said elongated horizontal member causing said frame to rotate about a second axis formed by a second diameter of said aperture, said second diameter being perpendicular to said first diameter;

said frame is disposed to align with said target and an x-ray beam passing through said aperture to reach said target when said aperture center overlies said target and said aperture appears as a circle on a display;

whereby alignment for said puncturing tool is provided by said aiming frame.

4. The apparatus as defined in claim 3, wherein said second rotating means is comprised of a first cog coupled to a second cog disposed along a second side of said bracket, said second cog being coupled to said bracket and for rotating said bracket about said proximal end of said elongated horizontal member.

5. The apparatus as defined in claim 4, wherein said elongated horizontal member includes a screw coupled through said coupler for providing said horizontal movement.

6. The apparatus as defined in claim 5, wherein said distal end of said elongated vertical member further including pivoting means for providing said distal end to pivot in relation to said mounting means which allows said apparatus to pivot about said fixed object.

7. The apparatus as defined in claim 6, further including a sighting element having opaque cross-hair lines for aligning said aperture center, said sighting element being adapted to be inserted in said aperture.

8. The apparatus as defined in claim 7, further including a holder for aligning and guiding said tool, said holder being adapted to be inserted in said aperture; said holder having a tube disposed therein, such that said tube is used to align said holder to said target.

9. The apparatus as defined in claim 8, wherein said tube is comprised of a metallic material.

* * * * *